(12) United States Patent
Liao

(10) Patent No.: US 9,009,903 B2
(45) Date of Patent: Apr. 21, 2015

(54) TOOTHBRUSH

(71) Applicant: Jin-Po Liao, Taichung (TW)

(72) Inventor: Jin-Po Liao, Taichung (TW)

( * ) Notice: Subject to any disclaimer, the term of this patent is extended or adjusted under 35 U.S.C. 154(b) by 194 days.

(21) Appl. No.: 13/924,276

(22) Filed: Jun. 21, 2013

(65) Prior Publication Data

US 2014/0373293 A1    Dec. 25, 2014

(51) Int. Cl.
*A46B 7/06* (2006.01)
*A46B 13/08* (2006.01)
*A46B 9/04* (2006.01)
*A61C 17/32* (2006.01)

(52) U.S. Cl.
CPC ... *A46B 9/04* (2013.01); *A46B 7/06* (2013.01); *A46B 13/08* (2013.01); *A61C 17/32* (2013.01)

(58) Field of Classification Search
CPC ...... A61C 17/32; A61C 17/34; A61C 17/349; A61C 17/22; A46B 7/06; A46B 7/08; A46B 13/02; A46B 13/00; A46B 13/08
USPC .......................................... 15/22.1, 22.2, 28
See application file for complete search history.

(56) References Cited

U.S. PATENT DOCUMENTS 2,660,745 A * 12/1953 Yusko ............................ 15/22.1
6,148,462 A * 11/2000 Zseng ............................ 15/22.1

* cited by examiner

*Primary Examiner* — Mark Spisich
*Assistant Examiner* — Andrew A Horton
(74) *Attorney, Agent, or Firm* — Shimokaji IP

(57) ABSTRACT

A toothbrush has a handle assembly, a brush-head assembly and a transmitting assembly. The brush-head assembly is slidably mounted in the handle assembly and has a sliding shaft and a swing head. The sliding shaft has two supporting portions mounted on the sliding shaft opposite to the handle assembly. The swing head is mounted on the supporting portions and has a toothed part. The transmitting assembly has a transmitting shaft. The transmitting shaft is rotatably inserted in the sliding shaft and has a longitudinal restriction relative to the sliding shaft. The transmitting shaft has a toothed portion engaging the toothed part. When the transmitting shaft is rotated, the swing head is driven to swing by the toothed part and the toothed portion to provide an improved cleaning effect.

16 Claims, 6 Drawing Sheets

TOOTHBRUSH

BACKGROUND OF THE INVENTION

1. Field of the Invention

The present invention relates to a toothbrush, and more particularly to a toothbrush that can improve a cleaning effect of the toothbrush without any electric power.

2. Description of Related Art

A conventional manual or electric toothbrush is applied for cleaning teeth of a user. The user can hold and move the toothbrush left and right or up and down relative to the teeth of the user to clean the teeth.

However, a cleaning effect of the manual toothbrush is insufficient due to an incorrect operation of the toothbrush or a poor brushing habit of the user. In addition, although a cleaning effect of the electric toothbrush is sufficient enough by rotating a brush head of the electric toothbrush, the manufacturing cost of the electric toothbrush is much higher than that of the manual toothbrush. Therefore, how to strike a balance between the manual toothbrush and the electric toothbrush needs to be considered and resolved.

SUMMARY OF THE INVENTION

The main objective of the present invention is to provide a toothbrush that can improve the cleaning effect without electric power comparing with a conventional manual toothbrush and the manufacturing cost of the toothbrush can be reduced comparing with a conventional electric toothbrush.

The toothbrush comprises a handle assembly, a brush-head assembly and a transmitting assembly. The handle assembly comprises a spiral structure mounted inside the handle assembly.

The brush-head assembly is slidably inserted into the handle assembly and comprises a sliding shaft and a swing head. The sliding shaft is elongated, is slidably inserted into the handle assembly and comprises a rear end inserted into the handle assembly, a front end that is opposite to the rear end, a top surface, and a brush-head recess formed from the top surface and adjacent to the front end of the sliding shaft. The sliding shaft further comprises two supporting portions mounted in the brush-head recess and facing each other, two pin holes being elongated, formed respectively along parts of a periphery of the sliding shaft and formed through the sliding shaft, and aligning with each other, and multiple fixing bristles mounted on the sliding shaft, located at the front end of the sliding shaft and on two sides of the brush-head recess.

The swing head is mounted on the supporting portions, is mounted swingingly in the brush-head recess and comprises a toothed part and multiple bristles. The toothed part is mounted on a bottom side of the swing head. The bristles are mounted on a top side of the swing head.

The transmitting assembly is mounted in the handle assembly and the brush-head assembly and comprises a transmitting shaft, a pin, a sliding block, and two elastic elements. The transmitting shaft is rotatably inserted into the sliding shaft and the handle assembly and comprises a front end located in the brush-head recess, a rear end opposite to the front end and located in the handle assembly, a spiral structure mounted on the rear end of the transmitting shaft and matching the spiral structure of the handle assembly, and a toothed portion mounted on the front end of the transmitting shaft and engaging with the toothed part. The pin is inserted through the transmitting shaft and the pin holes. The sliding block is mounted around and engages with the sliding shaft and is located in the handle assembly. The elastic elements are mounted around the sliding shaft, are located respectively on two sides of the sliding block and located in the handle assembly, wherein each elastic element abuts between the sliding block and the handle assembly.

Other objectives, advantages and novel features of the present invention will become more apparent from the following detailed description when taken in conjunction with the accompanying drawings.

DETAILED DESCRIPTION OF PREFERRED EMBODIMENT

Figure 1:
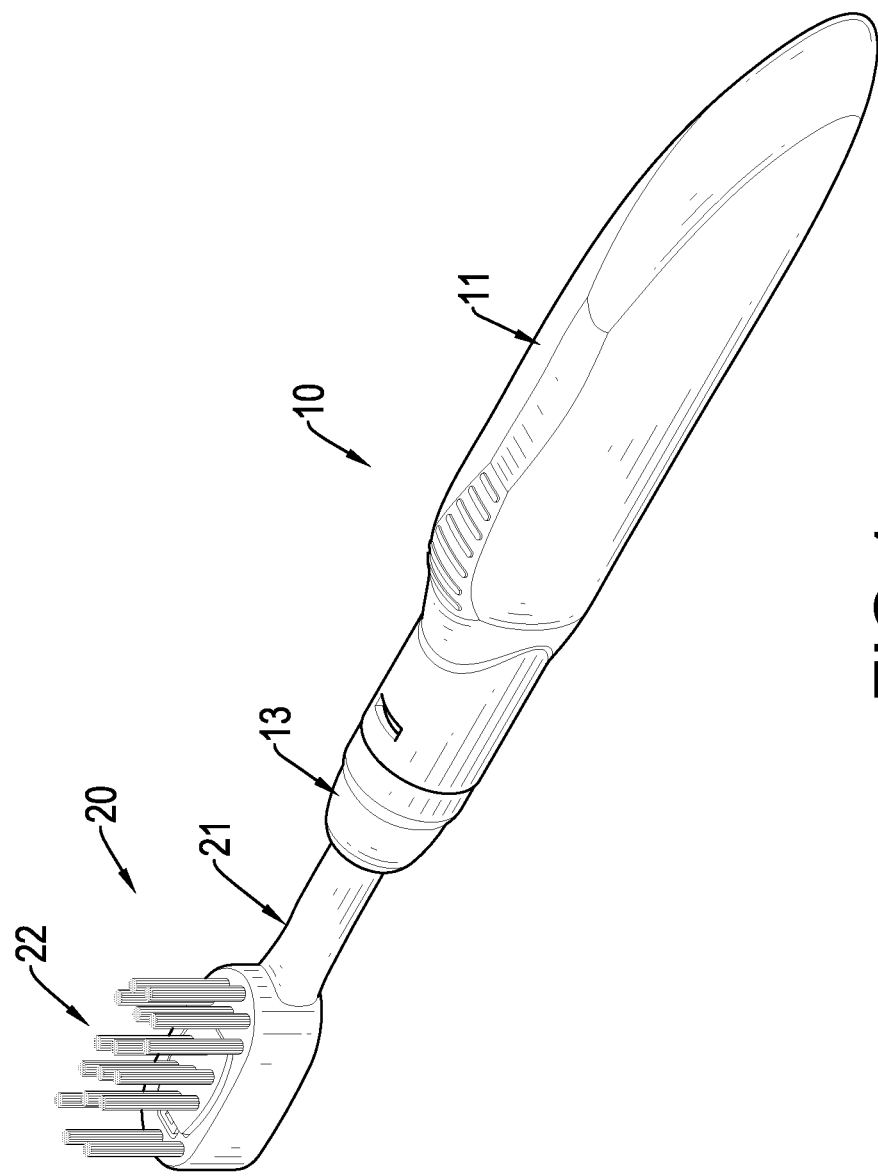
FIG. 1 is a perspective view of a preferred embodiment of a toothbrush in accordance with the present invention.

With reference to FIG. 1, a preferred embodiment of a toothbrush in accordance with the present invention comprises a handle assembly 10, a brush-head assembly 20, and a transmitting assembly 30.

Figure 2:
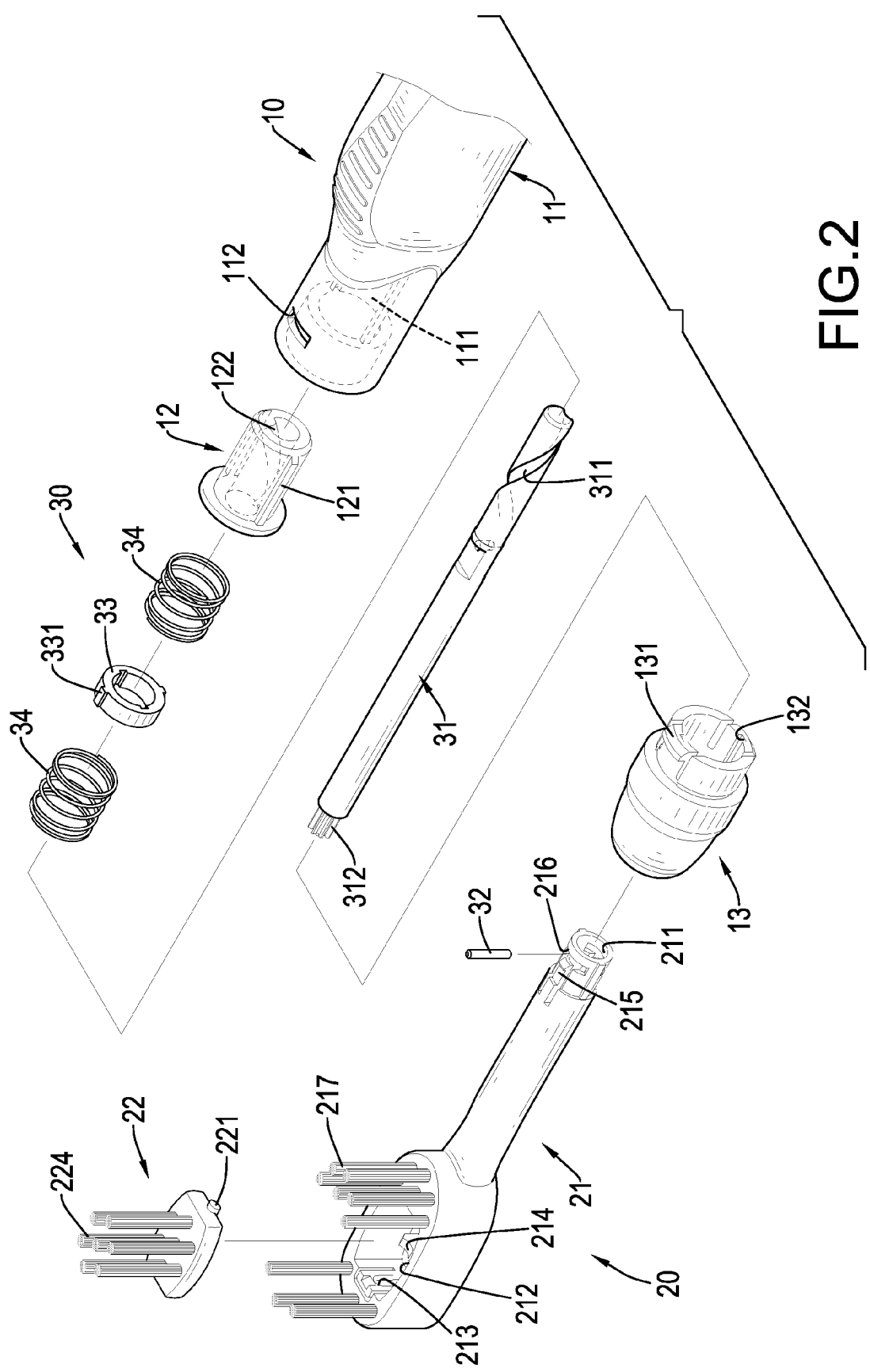
FIG. 2 is an enlarged exploded perspective view of the toothbrush in FIG. 1.

With reference to FIG. 2, the handle assembly 10 comprises a handle 11, a positioning tube 12, and a mounting tube 13. The handle 11 is provided to be held by a user and comprises a front end, a handle space 111 and two engaging recesses 112. The handle space 111 is formed in the handle 11 and comprises an opening that is formed at the front end of the handle 11. The engaging recesses 112 are formed through the handle 11, communicate with the handle space 111 and are adjacent to the opening of the handle space 111. The engaging recesses 112 align with each other. The positioning tube 12 is mounted in the handle space 111 from the opening of the handle space 111, abuts and engages with the front end of the handle 11. Preferably, the positioning tube 12 engages with an inner wall of the handle 11 by two ribs 121. The ribs 121 protrude from the positioning tube 12 such that an engaging structure is formed by the ribs 121 and the inner wall of the handle 11 to keep the positioning tube 12 from rotating relative to the handle 11. The positioning tube 12 comprises a spiral structure 122 mounted on an inner wall of the positioning tube 12. Preferably, the spiral structure 122 protrudes from the inner wall of the positioning tube 12.

The mounting tube 13 is inserted into the handle space 111, abuts the positioning tube 12 and engages the handle 11. The mounting tube 13 comprises a rear end, two engaging portions 131 and two slits 132. The rear end of the mounting tube 13 is inserted into the handle space 111 and abuts the positioning tube 12. The engaging portions 131 are mounted on the rear end of the mounting tube 13 and respectively engage the engaging recesses 112. The slits 132 are formed in an inner wall of the mounting tube 13 and are parallel with a longitudinal direction of the mounting tube 13.

Figure 3:
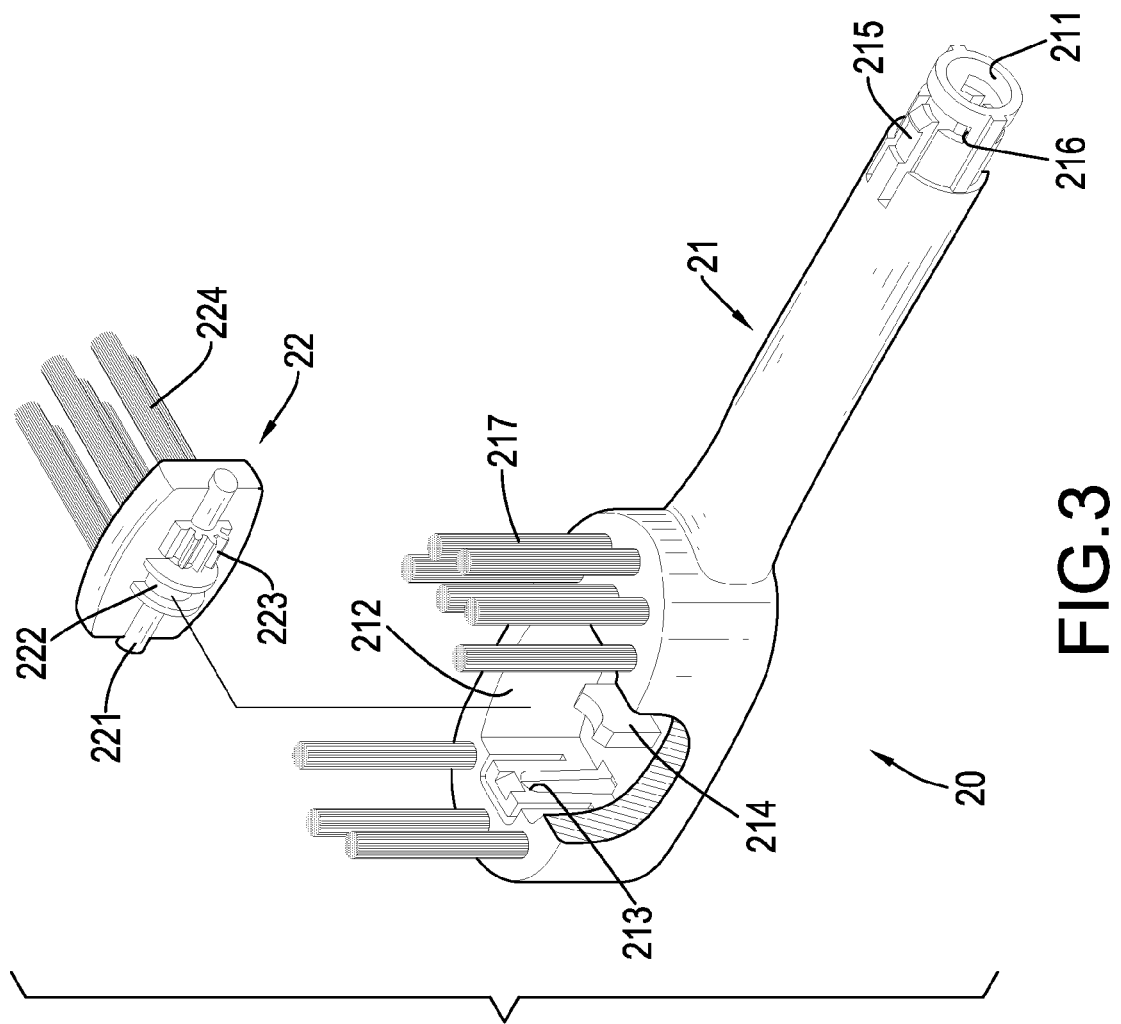
FIG. 3 is a partially enlarged exploded perspective view in partial section of the toothbrush in FIG. 1.
Figure 4:
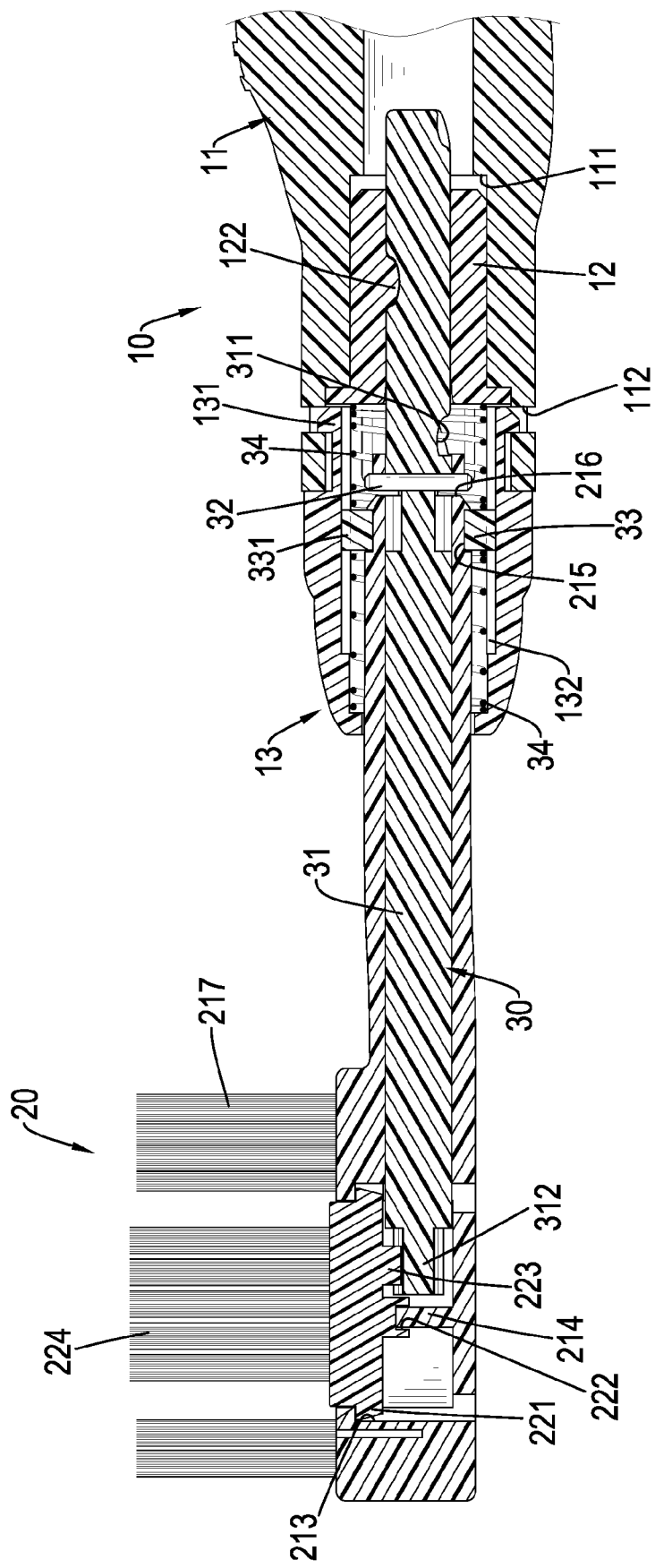
FIG. 4 is a partially enlarged cross sectional side view of the toothbrush in FIG. 1.

With reference to FIG. 3, the brush-head assembly 20 is inserted into the mounting tube 13 and is moveable relative to the handle assembly 10. The brush-head assembly 20 comprises a sliding shaft 21 and a swing head 22. The sliding shaft 21 is elongated, is slidably inserted into the mounting tube 13 and comprises a front end, a top surface, a shaft space 211, a brush-head recess 212, two supporting portions 213, a rail structure 214, a shaft recess 215, two pin holes 216 and multiple fixing bristles 217. The front end of the sliding shaft 21 is opposite to the mounting tube 13. The shaft space 211 is formed in and along the sliding shaft 21. The brush-head recess 212 is formed from the top surface of the sliding shaft 21, is adjacent to the front end of the sliding shaft 21 and communicates with the shaft space 211. The supporting portions 213 are mounted on an inner wall of the brush-head recess 212 and face each other. The rail structure 214 of the sliding shaft 21 is mounted on a bottom surface of the brush-head recess 212. Preferably, the rail structure 214 of the sliding shaft 21 is a block and the top end of the block is curved. The shaft recess 215 is annularly formed around an outer wall of the sliding shaft 21 and located in the mounting tube 13. The pin holes 216 are elongated, are formed through the sliding shaft 21 along the periphery of the sliding shaft 21 and align with each other. The pin holes 216 are adjacent to the shaft recess 215. The fixing bristles 217 are mounted on the sliding shaft 21 and located at two sides of the brush-head recess 212.

The swing head 22 is mounted in the brush-head recess 212 and comprises two supporting axles 221, a rail structure 222, a toothed part 223, and multiple bristles 224. The supporting axles 221 are mounted on the bottom side of the swing head 22 and protrude respectively from two ends of the swing head 22. The supporting axles 221 are mounted in the supporting portions 213 respectively. The rail structure 222 of the swing head 22 is mounted on the bottom side of the swing head 22 and matches the rail structure 214 of the sliding shaft 21. Preferably, the rail structure 222 of the swing head 22 is a rail and the bottom end of the rail is curved. The rail structure 222 of the swing head 22 engages with two sides of the rail structure 214 of the sliding shaft 21, such that the swing head 22 can be swung right and left relative to the sliding shaft 21 by the supporting axles 221. The toothed part 223 is mounted on the bottom side of the swing head 22 and teeth of the toothed part 223 are arranged in a curved pattern. The bristles 224 are mounted on a top side of the swing head 22.

With reference to FIGS. 2 and 3, the transmitting assembly 30 is mounted in the handle assembly 10 and the brush-head assembly 20 and comprises a transmitting shaft 31, a pin 32, a sliding block 33, and two elastic elements 34. The transmitting shaft 31 is rotatably inserted into the shaft space 211, the positioning tube 12 and the mounting tube 13. The transmitting shaft 31 comprises a front end, a rear end, a spiral structure 311 and a toothed portion 312. The front end of the transmitting shaft 31 is mounted in the brush-head recess 212 and the rear end of the transmitting shaft 31 is mounted in the positioning tube 12. The spiral structure 311 of the transmitting shaft 31 is mounted on the rear end of the transmitting shaft 31 and matches the spiral structure 122 of the positioning tube 12, such that the transmitting shaft 31 can be rotated relative to the positioning tube 12. The toothed portion 312 is mounted on the front end of the transmitting shaft 31 and engages with the toothed part 223, such that when the transmitting shaft 31 is rotated, the swing head 22 can be swung right and left with the engagement between the toothed portion 312 and the toothed part 223.

The pin 32 is mounted in the transmitting shaft 31 and the pin holes 216 to fix the position of the transmitting shaft 31 relative to the sliding shaft 21, such that the transmitting shaft 31 cannot be moved longitudinally relative to the sliding shaft 21. When the transmitting shaft 31 is rotated, the two ends of the pin 32 can be moved in the two pin holes 216, wherein the ends of the pin 32 protrudes out of the pin holes 216 respectively. The sliding block 33 is mounted around the sliding shaft 21 and engages in the shaft recess 215. The sliding block 33 comprises two engaging ribs 331. The engaging ribs 331 protrude from the sliding block 33 and are mounted in the slits 132 respectively. The elastic elements 34 are mounted around the sliding shaft 21 and are located in the mounting tube 13 and respectively on two sides of the sliding block 33. One of the elastic elements 34 abuts between the mounting tube 13 and the sliding block 33, and the other elastic element 34 abuts between the sliding block 33 and the positioning tube 12.

Figure 5:
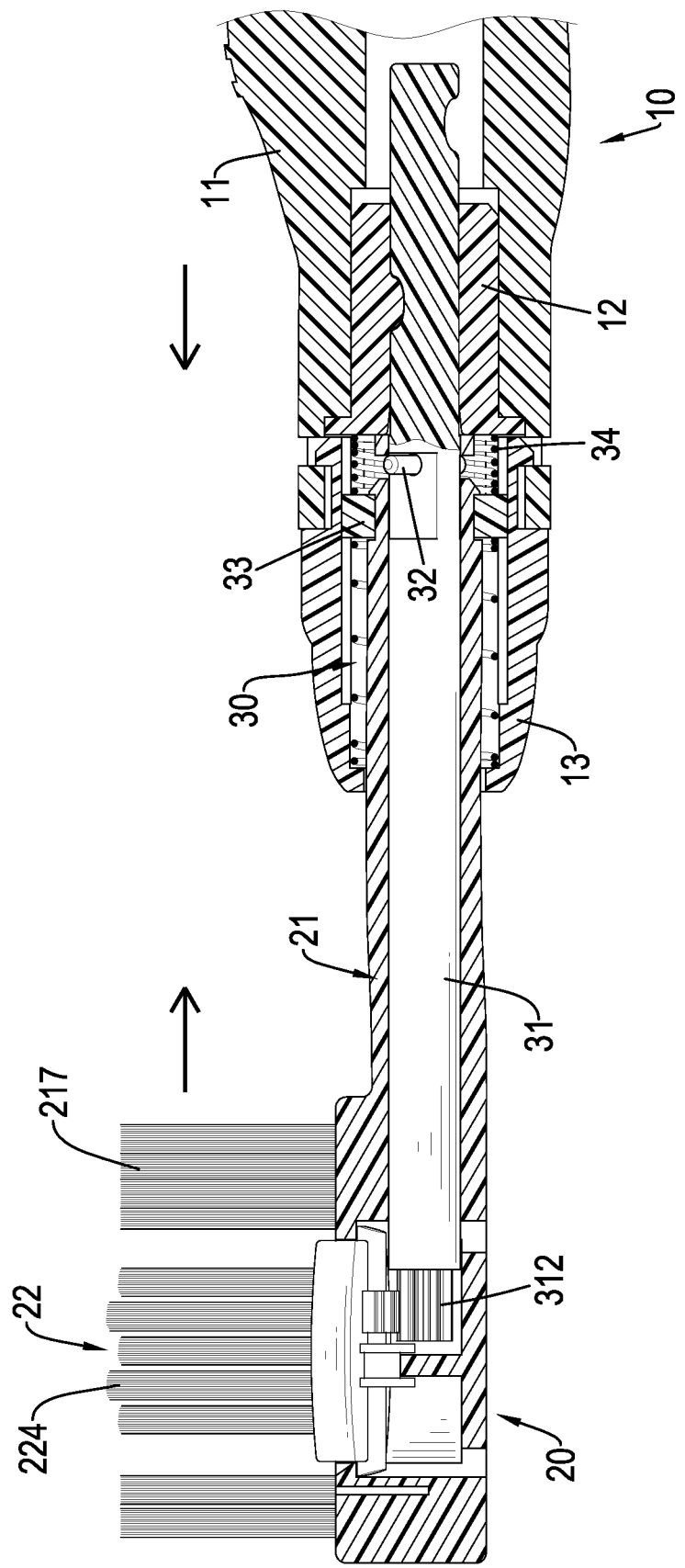
FIG. 5 is an operational and partially enlarged cross sectional side view of the toothbrush in FIG. 1.
Figure 6:
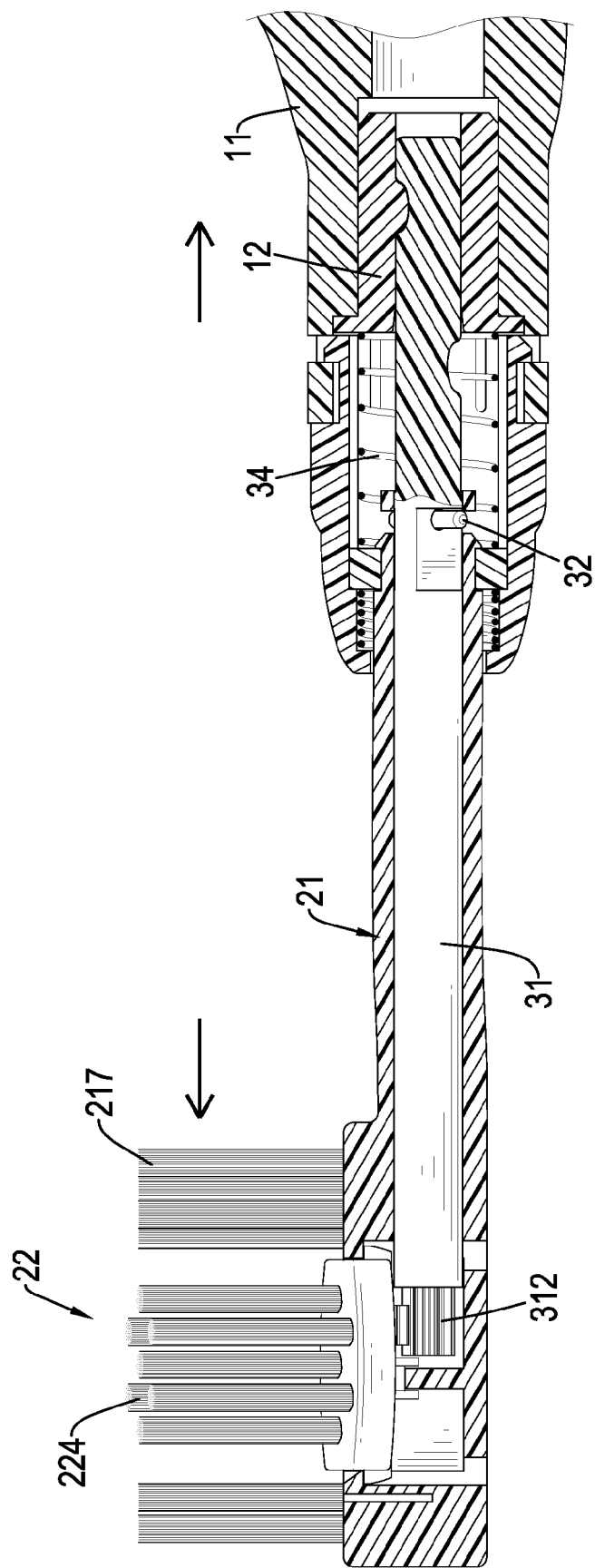
FIG. 6 is an operational and partially enlarged cross sectional side view of the toothbrush in FIG. 1.

With reference to FIGS. 2, 5 and 6, when a user holds the handle 11 to move in a leftward direction (as shown in FIG. 5) relative to teeth of the user, the brush-head assembly 20 is driven to move in a leftward direction by the handle assembly 10. The bristles 224 and the fixing bristles 217 abut against the cheek and the teeth of the user to provide a force to compress the sliding shaft 21, such that the sliding shaft 21 can be moved relative to the handle assembly 10 in an opposite direction (rightward direction as shown in FIG. 5). The transmitting shaft 31 can only be rotated, but not moved, relative to the sliding shaft 21 since the transmitting shaft 31 engages with the sliding shaft 21 by the pin 32 and the pin 32 is mounted in the pin holes 216. When the sliding shaft 21 is moved relative to the handle assembly 10 in an opposite direction, the transmitting shaft 31 is driven to move by the sliding shaft 21; in the meantime time, the transmitting shaft 31 is rotated due to the spiral structure 122 of the positioning tube 12 and the spiral structure 311 of the transmitting shaft 31. When the transmitting shaft 31 is rotated, the swing head 22 is driven to swing (inward direction as shown in FIG. 5) by the toothed portion 312.

On the other hand, when the user holds the handle 11 to move in a rightward direction (as shown in FIG. 6) relative to the teeth of the user, one of the elastic elements 34 that has been compressed in the original state (located at the right side of the sliding block 33 as shown in FIG. 5) pushes the sliding block 33 to move relative to the handle 11 in an opposite direction (leftward direction as shown in FIG. 6). The sliding shaft 21 is further driven to move by the sliding block 33 relative to the handle 11 in an opposite direction. The transmitting shaft 31 is driven to move by the sliding shaft 21. In the meantime, the transmitting shaft 31 is rotated relative to the positioning tube 12. Then, the swing head 22 is driven to swing (outward direction as shown in FIG. 6) by the toothed portion 312.

When the transmitting shaft 31 is rotated, the pin 32 is also rotated with the transmitting shaft 31 and each end of the pin 32 moves between the two ends of a corresponding pin hole 216 at position. When the two ends of the pin 32 are located at any two ends of the two pin holes 216, the pin 32 is blocked to stop by the sliding shaft 21. Then, the transmitting shaft 31 is also stopped rotating by the pin 32. In the meantime, one of the elastic elements 34 that has been compressed pushes the sliding block 33 to further push the sliding shaft 21. The transmitting shaft 31 moves with the sliding shaft 21 and is rotated relative to the positioning tube 12 to drive the swing head 22 to swing. Therefore, the swing head 22 can keep swinging (inward direction and outward direction as shown in FIGS. 5 and 6) when the handle 11 is held (leftward direction and right direction as shown in FIGS. 5 and 6) relative to the teeth of the user.

According to the above-mentioned operation, when the user holds the handle 11 to move rightward and leftward to clean the teeth, the fixing bristles 217 clean the teeth of the user in a linear motion (rightward and leftward) and the bristles 224 clean the teeth of the user in a swinging motion (upward and downward) to provide a three-dimensional cleaning effect and to improve the cleaning effect of the toothbrush. Furthermore, the manufacturing cost of the toothbrush can be reduced comparing with a conventional electric toothbrush and the user can use the toothbrush to clean teeth without electric power.

What is claimed is:

1. A toothbrush comprising:
   a handle assembly comprising a spiral structure mounted inside the handle assembly;
   a brush-head assembly slidably inserted into the handle assembly and comprising
      a sliding shaft being elongated, slidably inserted into the handle assembly and comprising
         a rear end inserted into the handle assembly;
         a front end opposite to the rear end;
         a top surface;
         a brush-head recess formed from the top surface and being adjacent to the front end of the sliding shaft;
         two supporting portions mounted in the brush-head recess and facing each other;
         two pin holes being elongated, formed respectively along parts of a periphery of the sliding shaft and formed through the sliding shaft, and the pin holes aligning with each other; and
         multiple fixing bristles mounted on the sliding shaft, located at the front end of the sliding shaft and on two sides of the brush-head recess; and
      a swing head mounted on the supporting portions, mounted swingingly in the brush-head recess and comprising
         a toothed part mounted on a bottom side of the swing head; and
         multiple bristles mounted on a top side of the swing head;
   a transmitting assembly mounted in the handle assembly and the brush-head assembly and comprising
      a transmitting shaft rotatably inserted into the sliding shaft and the handle assembly and comprising
         a front end located in the brush-head recess;
         a rear end opposite to the front end and located in the handle assembly;
         a spiral structure mounted on the rear end of the transmitting shaft and matching the spiral structure of the handle assembly; and
         a toothed portion mounted on the front end of the transmitting shaft and engaging with the toothed part;
      a pin inserted through the transmitting shaft and the pin holes;
      a sliding block mounted around and engaging with the sliding shaft and located in the handle assembly; and
      two elastic elements mounted around the sliding shaft, located respectively on two sides of the sliding block and located in the handle assembly, wherein each elastic element abuts between the sliding block and the handle assembly.

2. The toothbrush as claimed in claim 1, wherein the handle assembly comprises
   a positioning tube mounted around the transmitting shaft, wherein the spiral structure of the handle assembly is mounted on an inner wall of the positioning tube and the transmitting shaft is selectively rotated in the positioning tube by the spiral structure of the handle assembly and the spiral structure of the transmitting shaft; and
   a mounting tube mounted around the sliding shaft, the sliding block and the elastic elements, wherein one of the elastic elements abuts between the positioning tube and the sliding block, and the other elastic element abuts between the mounting tube and the sliding block.

3. The toothbrush as claimed in claim 2, wherein
   the swing head further comprises
      two supporting axles mounted on the bottom side of the swing head and respectively mounted in the supporting portions; and
      a rail structure mounted on the bottom side of the swing head; and
   the sliding shaft further comprises a rail structure mounted on a bottom surface of the brush-head recess of the sliding shaft, wherein the rail structure of the sliding shaft and the rail structure of the swing head are both curved and match each other.

4. The toothbrush as claimed in claim 3, wherein teeth of the toothed part of the swing head are mounted in a curved pattern.

5. The toothbrush as claimed in claim 4, wherein
   the rail structure of the sliding shaft is a block and a top end of the block is curved; and
   the rail structure of the swing head is a rail and a bottom end of the rail is curved.

6. The toothbrush as claimed in claim 2, wherein the sliding shaft further comprises a shaft recess concaved in the periphery of the sliding shaft, wherein the sliding block is mounted in and engages the shaft recess.

7. The toothbrush as claimed in claim 6, wherein
   the swing head further comprises
      two supporting axles mounted on the bottom side of the swing head and respectively mounted in the supporting portions; and
      a rail structure mounted on the bottom side of the swing head; and
   the sliding shaft further comprises a rail structure mounted on a bottom surface of the brush-head recess of the sliding shaft, wherein the rail structure of the sliding shaft and the rail structure of the swing head are both curved and match each other.

8. The toothbrush as claimed in claim 7, wherein teeth of the toothed part of the swing head are mounted in a curved pattern.

9. The toothbrush as claimed in claim 8, wherein
   the rail structure of the sliding shaft is a block and a top end of the block is curved; and
   the rail structure of the swing head is a rail and a bottom end of the rail is curved.

10. The toothbrush as claimed in claim 6, wherein
    the mounting tube comprises two slits concaved in an inner wall of the mounting tube and parallel with a longitudinal direction of the mounting tube; and
    the sliding block comprises two engaging ribs protruding on an outer wall of the sliding block and respectively mounted in the slits.

11. The toothbrush as claimed in claim 10, wherein
    the swing head further comprises
       two supporting axles mounted on the bottom side of the swing head and respectively mounted in the supporting portions; and
       a rail structure mounted on the bottom side of the swing head; and
    the sliding shaft further comprises a rail structure mounted on a bottom surface of the brush-head recess of the sliding shaft, wherein the rail structure of the sliding shaft and the rail structure of the swing head are both curved and match each other.

12. The toothbrush as claimed in claim 11, wherein teeth of the toothed part of the swing head is mounted in a curved pattern.

13. The toothbrush as claimed in claim 12, wherein
the rail structure of the sliding shaft is a block and a top end of the block is curved; and
the rail structure of the swing head is a rail and a bottom end of the rail is curved.

14. The toothbrush as claimed in claim 1, wherein
the swing head further comprises
two supporting axles mounted on the bottom side of the swing head and respectively mounted in the supporting portions; and
a rail structure mounted on the bottom side of the swing head; and
the sliding shaft further comprises a rail structure mounted on a bottom surface of the brush-head recess of the sliding shaft, wherein the rail structure of the sliding shaft and the rail structure of the swing head are both curved and match each other.

15. The toothbrush as claimed in claim 14, wherein teeth of the toothed part of the swing head are mounted in a curved pattern.

16. The toothbrush as claimed in claim 15, wherein
the rail structure of the sliding shaft is a block and a top end of the block is curved; and
the rail structure of the swing head is a rail and a bottom end of the rail is curved.

* * * * *